United States Patent
Szeles et al.

(10) Patent No.: US 7,402,416 B2
(45) Date of Patent: Jul. 22, 2008

(54) ANTIBACTERIAL DENTIFRICE EXHIBITING ANTIPLAQUE AND BREATH FRESHENING PROPERTIES

(75) Inventors: Lori H. Szeles, Howell, NJ (US); Xiaoyan Liu, Highland Park, NJ (US); Malcolm Williams, Piscataway, NJ (US); James G. Masters, Ringoes, NJ (US)

(73) Assignee: Colgate-Palmolive Company, New York, NY (US)

(*) Notice: Subject to any disclaimer, the term of this patent is extended or adjusted under 35 U.S.C. 154(b) by 1587 days.

(21) Appl. No.: 10/143,395

(22) Filed: May 10, 2002

(65) Prior Publication Data

US 2003/0211054 A1 Nov. 13, 2003

(51) Int. Cl.
*C12N 9/00* (2006.01)
(52) U.S. Cl. ..................................................... 435/183
(58) Field of Classification Search ................... 424/50; 435/183, 198, 205
See application file for complete search history.

(56) References Cited

U.S. PATENT DOCUMENTS

| | | | | |
|---|---|---|---|---|
| 3,751,561 | A | * | 8/1973 | Wildi et al. .................. 424/48 |
| 4,537,764 | A | * | 8/1985 | Pellico et al. |
| 5,178,869 | A | * | 1/1993 | Ebine et al. |
| 5,820,853 | A | * | 10/1998 | Glandorf |
| 5,891,422 | A | * | 4/1999 | Pan et al. |
| 6,379,654 | B1 | * | 4/2002 | Gebreselassie et al. |

FOREIGN PATENT DOCUMENTS

| | | | |
|---|---|---|---|
| BE | 439463 | * | 9/1963 |
| BE | 755331 | * | 4/1974 |
| ES | 2158773 | * | 9/2001 |
| GB | 1265468 | * | 3/1972 |

* cited by examiner

*Primary Examiner*—Michael V Meller
(74) *Attorney, Agent, or Firm*—Donald L. Traut

(57) ABSTRACT

A dual component antiplaque oral composition having antimalodor properties in which a first component contains an antibacterial agent and the second component contains a proteolytic enzyme, the first and second components are simultaneously combined for application to the teeth, the first and second components being physically segregated prior to use, the components when mixed upon application to teeth providing substantially antiplaque effect with superior antimalodor properties.

8 Claims, No Drawings

ANTIBACTERIAL DENTIFRICE EXHIBITING ANTIPLAQUE AND BREATH FRESHENING PROPERTIES

BACKGROUND OF THE INVENTION

1. Field of the Invention

The present invention relates to an oral care composition which contains a nonionic antibacterial compound effective in retarding bacterial plaque accumulation on teeth and more particularly to a dual component dentifrice composition containing an antibacterial compound in combination with an enzyme which achieves plaque reduction with superior breath freshening characteristics.

2. The Prior Art

Halitosis, the technical term for bad breath, or Fetor ex Oris, is an undesirable condition. As a matter of fact, everyone, excluding the very young, occasionally has bad breath, with approximately 25% suffering on a regular basis and the problem tends to get worse and more frequent as one gets older. The problem seems to be evenly split between men and women. Bad breath results when proteins from the food we eat and saliva debris are broken down by bacteria. Even the cleanest mouth hosts millions of bacteria which have the potential to decompose these protein-containing particles left in the mouth. The tongue, with its fissures and large, bumpy surface area, retains considerable quantities of food and debris that support and protect a large bacterial population. Under low oxygen condition, this bacterial population forms foul smelling products, called volatile sulfur compounds (VSC)—such as hydrogen sulfide ("rotten eggs") and methyl mercaptans ("skunk smell") and other odorous and bad tasting compounds. Up to 80-90% of bad breath that originates in the mouth is by this mechanism.

Dental plaque or plaque bio-film is a soft deposit that forms on teeth and is comprised of an accumulation of bacteria and salivary as well as food by-products. Plaque adheres tenaciously at the points of irregularity or discontinuity, e.g., on rough calculus surfaces, at the gum line, on tongue surface and within crevices, and the like. Besides being unsightly, plaque is implicated in the occurrence of gingivitis and other forms of periodontal disease.

Bacteria thrive on the tongue. For the most part, the bacteria are a part of a protective bio-film that essentially renders them resistant to most treatments. Few people clean their tongue after brushing, even though it's been shown that as much as 50 percent of the mouth's bacteria can be found here. Additionally, for many people, brushing or scraping the tongue is difficult because of the gag reflex. Therefore, cleaning the tongue non-mechanically is highly desirable for those who are unable to do so with a mechanical device.

A wide variety of antibacterial agents have been suggested in the art to retard plaque formation and the oral infections and dental disease associated with plaque formation. For example, nonionic antibacterial compounds such as Triclosan are well known to the art for their antibacterial activity and have been used in oral compositions to counter plaque formation by bacterial accumulation in the oral cavity.

In spite of the extensive prior art relating to antibacterial dentifrice compositions, there is still a need in the art to formulate a dentifrice product capable of delivering an antibacterial agent effective in the retardation of bacterial plaque accumulation on teeth, as well as on the tongue, without inhibiting the bioavailability of the antibacterial compound. The delivery of the antibacterial compound to the tongue will allow for effective control of bad breath.

SUMMARY OF THE INVENTION

The present invention encompasses a dual component dental composition which when applied to teeth contains a combination of a nonionic antibacterial compound, and an enzyme ingredient whereby reduction of plaque accompanied by a superior antimalodor benefit is accomplished during tooth brushing.

The present invention is based upon the discovery that when a separately maintained first nonionic antibacterial compound containing dental component and a second enzyme containing dentifrice component are simultaneously combined and thereafter applied to the surface of the teeth, undiminished antiplaque efficacy is unexpectedly obtained with a superior retardation of oral cavity malodor when the teeth are brushed with the combined components.

In one embodiment of the present invention, a dual component dentifrice composition of the present invention is provided being comprised of separate nonionic antibacterial compound and enzyme containing dentifrice components which are housed in a container wherein the components are maintained separate from each other and are not combined and admixed until simultaneous application to teeth is to be performed by the user as by brushing. Unexpectedly, when the separately maintained dental components are contacted with each other immediately prior to application to teeth, there is obtained undiminished antiplaque efficacy of the nonionic antibacterial compound accompanied by an enhanced antimalodor benefit.

The dual component dentifrice composition of the present invention was found to significantly reduce total bacteria on the tongue. Even more specifically, this dual component dentifrice combination was found to significantly reduce the level of bacterial species on the tongue surface responsible for the evolution of oral malodor up to five hours post brushing when compared to a clinically proven commercial toothpaste containing Triclosan.

DESCRIPTION OF THE PREFERRED EMBODIMENTS

Nonionic Antibacterial Agent

Nonionic antibacterial agents used in the practice of the present invention include halogenated diphenyl ether compounds such as 2,4,4'-trichloro-2'-hydroxydiphenyl ether (Triclosan) and 2,2'-dihydroxy-5,5'-dibromodiphenyl ether. Other useful nonionic antibacterial agents include phenolic compounds including phenol and its homologs, mono and polyalkyl and aromatic halophenols, resorcinol and its derivatives and bisphenolic compounds, such phenolic compounds being more fully disclosed in U.S. Pat. No. 5,368,844, the disclosure of which is incorporated herein by reference.

The nonionic antibacterial agent is included in the dentifrice composition at a concentration of about 0.10 to about 1.5% by weight and preferably about 0.3 to about 1.2% by weight.

Abrasives

Abrasives preferred for use the practice of the present invention include silica materials and particularly silica gels and precipitated amorphous silica having an oil absorption value of less than 100 cc/100 g silica and preferably in the range of from about 45 cc/100 g to less than about 70 cc/100 g silica. These silicas are colloidal particles having an average particle size ranging from about 3 microns to about 12 microns, and more preferably between about 5 to about 10 microns and a pH range from 4 to 10 preferably 6 to 9 when measured as a 5% by weight slurry.

Oil absorption values are measured using the ASTM Rub-Out Method D281. The low oil absorption silica abrasive is present in the oral care compositions of the present invention at a concentration of about 5 to about 40% by weight and preferably about 10 to about 30% by weight.

Low oil absorption silica abrasives particularly useful in the practice of the present invention are marketed under the trade designation Sylodent XWA by Davison Chemical Division of W. R. Grace & Co., Baltimore, Md. 21203. Sylodent 650 XWA, a silica hydrogel composed of particles of colloidal silica having a water content of 29% by weight averaging from about 7 to about 10 microns in diameter, and an oil absorption of less than 70 cc/100 g of silica is a preferred example of a low oil absorption silica abrasive useful in the practice of the present invention.

Another low oil absorption silica abrasive particularly useful in the practice of the present invention is marketed under the trade designation DP-105 by J. M. Huber Chemicals Division, Havre de Grace, Md. 21078 is a precipitated amorphous silica having an average particle size distribution from 5 to 12 microns and an oil absorption in the range of 50 to 70 cc/100 g.

Other abrasives which may be used in the practice of the present invention include precipitated silicas having a mean particle size of up to about 20 microns, such as Zeodent 115, marketed by J. M. Huber Chemicals Division, Havre de Grace, Md. 21078, or Sylodent 783 marketed by Davison Chemical Division of W. R. Grace & Company, sodium metaphosphate, potassium metaphosphate, tricalcium phosphate, dihydrated dicalcium phosphate, aluminum silicate, calcined alumina, bentonite or other siliceous materials, or combinations thereof.

The abrasive materials may be used individually as the sole abrasive in preparing the dental composition of the present invention or in combination with other known dentifrice abrasives. The total quantity of abrasive present in the dentifrice compositions of the present invention is at a level of from about 5% to about 60% by weight, preferably from about 10% to about 55% by weight when the dentifrice composition is a toothpaste.

Enzymes

The enzymes useful in the practice of the present invention include protein substances within the class of proteases, which breakdown or hydrolyze proteins (proteases). These proteolytic enzymes are obtained from natural sources or by the action of microorganisms having a nitrogen source and a carbon source. Examples of proteolylic enzymes useful in the practice of the present invention include papain, bromelain, chymotrypsin, ficin and alcalase.

Papain obtained from the milky latex of the Papaya tree is the proteolytic enzyme preferred for use in the practice of the present invention and is incorporated in the oral care composition of the present invention in an amount of about 0.1 to about 10% by weight and preferably about 0.5 to about 5% by weight, such papain having an activity of 150 to 300 MCU per milligram as determined by the Milk Clot Assay Test of the Biddle Sawyer Group (see J. Biol. Chem., vol. 121, pages 737-745).

An additional enzyme which is formulated in combination with the protease enzyme papain is glucoamylase. Glucoamylase is a saccharifying glucoamylase of *Aspergillus niger* origin cultivated by fermentation. This enzyme can hydrolyze both the alpha-D-1,6 glucosidic branch points and the alpha-1,4 glucosidic bonds of glucosyl oligosaccharides.

The product of this invention comprises about 0.001 to 2% of the carbohydrase and preferably about 0.01 to 0.55% by weight. Additional carbohydrases useful in accordance with this invention are glucoamylase, alpha and beta-amylase, dextranase and mutanase.

Other enzymes which may be used in the practice of the present invention include other carbohydrases such as alpha-amylase, beta-amylase, dextranase and mutanase and lipases such as plant lipase, gastric lipase, pancreatic lipase, pectinase, tannase lysozyme and serine proteases.

The lipase enzyme is derived from a select strain of *Aspergillus niger*, exhibiting random cleaving of the 1,3 positions of fats and oils. The enzyme has maximum lipolytic activity at pH 5.0 to 7.0 when assayed with olive oil. The lipase may be included in the dentifrice composition at a concentration of about 0.010 to about 5.0% by weight and preferably about 0.02 to about 0.10% by weight.

The presence of tannase enzyme can be further beneficial in facilitating the breakdown of extrinsic stain. Tannase enzymes have been purified from *Aspergillus niger* and *Aspergillus allianceus* and are useful in the hydrolysis of tannins, known to discolor the tooth surface.

Other suitable enzymes which can comprise the present invention include lysozyme, derived from egg white, which contains a single polypeptide chain crosslinked by four disulfide bonds having a molecular weight of 14,600 daltons. The enzyme can exhibit antibacterial properties by facilitating the hydrolysis of bacterial cell walls cleaving the glycosidic bond between carbon number 1 of N-acetylmuramic acid and carbon number 4 of N-acetyl-D-glucosamine, which in vivo, are polymerized to form the cell wall polysaccharide. Additionally, pectinase, an enzyme that is present in most plants, facilitates the hydrolysis of the polysaccharide pectin into sugars and galacturonic acid.

Dentifrice Vehicle

The orally-acceptable dentifrice vehicle used to prepare the dentifrice composition comprises a water-phase, containing a humectant therein. The humectant is preferably glycerin, sorbitol, xylitol, and/or propylene glycol of molecular weight in the range of 200 to 1,000. Other humectants, such as polyethylene glycol, and mixtures thereof may also be employed. The humectant concentration typically totals about 5 to about 70% by weight of the oral composition.

Reference hereto to sorbitol refers to the material typically commercially available as a 70% aqueous solution. Water is present typically in amount of at least about 10% by weight, and generally about 15 to 30% by weight of the oral composition. Water employed in the preparation of commercially suitable toothpastes should preferably be deionized and free of organic impurities. These amounts of water include the free water which is added plus that which is introduced with other materials such as with sorbitol.

The dentifrice compositions of the present invention can contain a variety of optional dentifrice ingredients. As described below, such optional ingredients can include, but are not limited to, thickening agents, surfactants, antitartar agents, a source of fluoride ions, a synthetic anionic polycarboxylate, a flavoring agent, antitartar and coloring agents.

Thickening Agents

Thickeners used in the compositions of the present invention include natural and synthetic gums and colloids. Suitable thickeners include naturally occurring polymers such as carrageenans, xanthan gum, polyglycols of varying molecular weights sold under the tradename Polyox, and polyvinylpyrrolidone. Compatible inorganic thickeners include amorphous silica compounds which function as thickening agents and include colloidal silicas compounds available under the trade designation Cab-o-sil manufactured by Cabot Corporation and distributed by Lenape Chemical, Bound Brook, N.J.; Zeodent 165 from J. M. Huber Chemicals Division, Havre de Grace, Md. 21078; and Sylodent 15, available from Davison Chemical Division of W. R. Grace Corporation, Baltimore, Md. 21203. Other inorganic thickeners include natural and synthetic clays such as hectorite clays, lithium magnesium silicate (laponite) and magnesium aluminum silicate (Veegum).

The thickening agent is present in the dentifrice composition in amounts of about 0.1 to about 10% by weight, preferably about 0.5 to about 4.0% by weight.

Surfactants

Surfactants are used in the compositions of the present invention to achieve increased prophylactic action and render the dentifrice compositions more cosmetically acceptable. The surfactant is preferably a detersive material that imparts to the composition detersive and foaming properties.

Anionic surfactants such as higher alkyl sulfates such as sodium lauryl sulfate are not compatible with enzymes. Anionic surfactants denature enzyme and cause loss of activity. As a result, it is important to the practice of the present invention to use a surfactant or combination of surfactants that are compatible with the enzymes present in the toothpaste formulation and provide the requisite foaming characteristics. Examples of enzyme compatible surfactants include nonanionic polyoxyethylene surfactants such as Pluronic F127, Polyoxamer 407, Steareth 30, Polysorbate 20, and amphoteric surfactants such as cocamidopropyl betaine and cocamidopropyl betaine lauryl glucoside. Preferred surfactants include a combination of pluronic F127, Polyoxamer 407, Polysorbate 20, and cocamidopropyl betaine at a total surfactant concentration in the dentifrice composition of between about 2 to about 10% by weight and preferably between about 3.5 to about 6.5% by weight at weight ratios of 2.5 Polyaxomer 407, 2.5 PEG-40 castor oil, 3.3 Polysorbate-20 and 1.0 cocamidopropyl betaine.

Fluoride and Other Active Agents

The dentifrice composition of the present invention may also contain a source of fluoride ions or fluorine-providing component, as anticaries agent in amount sufficient to supply about 25 ppm to 5,000 ppm of fluoride ions and include inorganic fluoride salts, such as soluble alkali metal salts. For example, preferred fluoride sources which are compatible with enzymes present in the composition are sodium fluoride, potassium fluoride, sodium fluorosilicate, ammonium fluorosilicate, as well as tin fluorides, such as stannous fluoride and stannous chloride. Sodium fluoride is preferred.

In addition to fluoride compounds, there may also be included antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$ sodium tripolyphosphate, long chain polyphosphates such as sodium hexametaphosphate and cyclic phosphates such as sodium trimetaphosphate. These antitartar agents are included in the dentifrice composition at a concentration of about 1 to about 5% by weight.

Enzyme Stabilizing Agents

The dentifrice composition of the present invention may also contain ingredients that stabilize enzymes in a dentifrice environment. These stabilizers protect the enzyme from inactivation by chelating metal impurities present in the dentifrice composition. Chelating agents include, ethylene diamine tetraacetic acid (EDTA) and sodium gluconate at concentrations between 0.01 and 1%, preferably between 0.1 and 0.5%. Other stabilizers may also prevent oxidation of amino acids, such as cysteine, that are critical for enzyme activity. Examples of agents that stabilize the enzyme against oxidation include sodium bisulfite, metal gallates, sodium stannate and ascorbic acid at concentrations between about 0.1 and about 1.5%, preferably between about 0.3 and about 0.75%.

Anionic Polycarboxylate

Synthetic anionic polycarboxylates may also be used in the dentifrice compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water-soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000 most preferably about 30,000 to about 700,000. Examples of these copolymers are available from GAF Corporation under the tradename Gantrez, e.g. AN 139 (M.W. 500,000), AN 119 (M.W. 250,000); S-97 Pharmaceutical Grade (M.W. 700,000), AN 169 (M.W. 1,200,000-1,800,000), and AN 179 (M.W. above 1,800,000); wherein the preferred copolymer is S-97 Pharmaceutical Grade (M.W. 700,000).

When present, the anionic polycarboxylates is employed in amounts effective to achieve the desired enhancement of the efficacy of any antibacterial, antitartar or other active agent within the dentifrice composition. Generally, the anionic polycarboxylates is present within the dentifrice composition from about 0.05% to about 4% by weight, preferably from about 0.5% to about 2.5% by weight.

Flavor

The dentifrice composition of the present invention may also contain a flavoring agent. Flavoring agents that are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

The flavoring agent is incorporated in the dentifrice composition at a concentration of about 0.1 to about 5% by weight and preferably about 0.5 to about 1.5% by weight.

Other Ingredients

Various other materials may be incorporated in the dentifrice compositions of this invention, including desensitizers, such as potassium nitrate; whitening agents; preservatives; silicones; and chlorophyll compounds. These additives, when present, are incorporated in the dentifrice composition in amounts which do not substantially adversely affect the properties and characteristics desired.

A striped dentifrice product is obtained in accordance with the practice of the present invention wherein colorants of contrasting colors are incorporated in each of the dentifrice components used in the practice of the present invention, the colorants being pharmacologically and physiologically non-toxic when used in the suggested amounts. Colorants used in the practice of the present invention include pigments and dyes.

To prepare the separate dentifrice components of the present invention, for example as in the preparation of the dentifrice component containing the nonionic antibacterial compound, the humectant and polymer binder are dispersed in a conventional mixer until the mixture becomes a well dispersed slurry which is smooth in appearance, after which water is added. This mixture is heated to 100-130° F. and mixed for 10 to 30 minutes producing a homogeneous gel phase. Sweetener and color are added and mixed for 20 minutes. The mixture is transferred to a vacuum mixer and the abrasive is added and mixed for 10 to 30 minutes at high speed under a vacuum in the range of 5 to 100 millimeter of mercury pressure, preferably 5 to 50 mm Hg, providing a homogeneous mixture. As the final stage the flavor and antibacterial compound are added followed by an additional 20 minute mixing under vacuum.

For the preparation of the enzyme containing dentifrice component, the polymeric binder is dispersed in humectant to form a smooth dispersed slurry. To this dispersion is added water, containing dissolved synthetic clay, salts and the sweetener. The resulting continuous phase is mixed under high speed for a period of no less than 20 minutes. To the resulting homogeneous continuous phase, silica abrasive is slowly added, along with the thickening silica and mixed under vacuum in the range of 5 to 100 mm of mercury for a period of 20 minutes. At this stage, the color, surfactants and enzyme ingredients are added and mixed under high speed for 10 to 20 minutes under a vacuum of 5 to 50 mm10 Hg. The flavor oils are then added to the mixture which is followed by mixing another 10 to 20 minutes under vacuum of 5 to 50 mm 10 Hg.

The resultant components are dentifrice compositions of a texture like that of normal toothpastes having a pH in the range of 5 to 8, preferably 6.5 to 7.5, e.g., 7, and of satisfactory flavor.

Packaging of the Dual Component Dentifrice

The dual component composition of the present invention is packaged in a suitable dispensing container such as a tube or pump in which the components are maintained physically separated and from which the separated components may be dispensed synchronously. Such containers are known to the art. Examples of suitable pump devices are disclosed in U.S. Pat. Nos. 4,528,180 and 5,332,124. Examples of a suitable dispensing tube are disclosed in U.S. Pat. Nos. 4,487,757 and 4,687,663 wherein the tube is formed from a collapsible plastic web and is provided with a partition within the tube defining separate compartments in which the physically separated components are stored and from which they are dispersed through a suitable dispensing outlet.

The following specific Example illustrates the present invention. The individual dentifrice components described below were prepared by following the procedure described above. The amounts of the various ingredients are by weight unless otherwise indicated. The resultant components were packaged in tubes or other containers provided with means for physical separation of the individual dentifrice components.

EXAMPLE I

A dual component dentifrice composition having the following ingredients was prepared:

| Component A | | Component B | |
|---|---|---|---|
| Ingredients | Wt. % | Ingredients | Wt. % |
| Deionized water | 10.079 | Deionized water | 16.0 |
| Sodium fluoride | 0.486 | Sodium MFP | 0.76 |
| Sodium saccharine | 0.25 | Sodium saccharin | 0.40 |
| Iota-carrageenan | 0.735 | Sorbitol (70%) | 19.25 |
| Titanium dioxide | 0.50 | Glycerin | 20.30 |
| Sorbitol (70%) | 8.00 | Sodium tripolyphosphate | 3.00 |
| Glycerin | 17.00 | Xanthan | 0.50 |
| Gantrez | 27.20 | Laponite D | 0.70 |
| NaOH 50% solution | 2.00 | Zeodent-115 | 5.00 |
| Zeodent-165 | 2.00 | Zeodent-165 | 2.00 |
| Zeodent-115 | 18.65 | Sylodent XWA650 | 20.00 |
| Flavor | 1.00 | Flavor | 1.10 |
| Sodium bicarbonate | 10.00 | Tetrasodium pyrophosphate | 2.00 |
| Triclosan | 0.60 | Titanium dioxide | 0.4 |
| Sodium lauryl sulfate | 1.50 | Tegobetaine | 2.00 |
| | | Polysorbate 20 | 2.00 |
| | | Polyethylene glycol 600 | 3.00 |
| | | Papain | 1.00 |
| | | Glucoamylase | 0.20 |
| | | Lipase | 0.06 |
| | | Sodium bisulfite | 0.10 |
| | | Sodium phosphate monobasic | 0.03 |
| | | Anhy. Na Phosphate dibasic | 0.20 |
| Total | 100.00 | | 100.00 |

Upon use, Components A and B are combined, for example on the toothbrush, to give a combined composition, designated as Composition "X". Composition "X" was evaluated for its ability to control bacteria on the back of the tongue that are responsible for oral malodor formation as well as the control of breath VSC using the Halimeter™.

The evaluation of the quantity of bacteria responsible for oral malodor was determined in-vivo in a tongue micro-flora study. The compositions were tested for their ability to reduce the micro-flora on the back of the tongue, especially those species responsible for the generation of $H_2S$. The study required panelists to swab one side of the back of the tongue for bacterial collection at baseline and the alternate back side of the tongue four hours post treatment. This was done before (baseline) and after panelists brushed with treatment products for 1 minute followed by swishing with the dentifrice slurry for 15 seconds. The collected samples were plated onto lead acetate agar media for the selection of $H_2S$-forming bacteria as well as blood agar media to determine the total level of bacteria present on the tongue and incubated under anaerobic conditions at 37° C. After 72 hours, colony-forming units of $H_2S$-forming bacteria, and total bacterial colony-forming units were enumerated. The mean colony forming unit results were used to calculate percent reduction from baseline.

The results of the in-vivo tongue micro-flora study are recorded in Table I below. For purposes of comparison a clinically proven commercial toothpaste product, containing 0.3% Triclosan, designated Composition "C", which did not contain enzymes, was also evaluated in the study. A placebo dentifrice which did not contain enzymes or Triclosan was also prepared containing a silica abrasive and SLS surfactant. The comparative and placebo dentifrice results are also recorded in Table I below.

TABLE I

TOTAL BACTERIA REDUCTION FROM TONGUE SURFACE

| Composition | Baseline Mean CFU* | 5 Hours Post Brushing Mean CFU | % Reduction from baseline of Mean CFU |
|---|---|---|---|
| Placebo | $6.2 \times 10^5$ | $5.4 \times 10^5$ | 14 |
| C | $3.7 \times 10^5$ | $1.4 \times 10^5$ | 63 |
| X | $1.2 \times 10^6$ | $1.2 \times 10^5$ | 89 |

CPU = Colny forming units

The results recorded in Table I indicate that the dentifrice composition of the present invention, Composition X unexpectedly provided a substantially reduced quantity of tongue bacteria as compared to the placebo and the comparative dentifrice, Composition C, a clinically proven Triclosan containing commercial product.

EXAMPLE II

The tongue micro-flora study procedure of Example I was also done to evaluate the ability of Composition "X" to specifically reduce odor-forming ($H_2S$) bacteria on the back of the tongue.

The results of this second study are recorded in Table II below.

TABLE II

$H_2S$-FORMING BACTERIA REDUCTION FROM TONGUE SURFACE

| Composition | Baseline Mean CFU | 5 Hours Post Treatment Mean CFU | % Reduction from Baseline |
|---|---|---|---|
| Placebo | $9.8 \times 10^4$ | $5.1 \times 10^4$ | 48 |
| C | $2.4 \times 10^5$ | $8.8 \times 10^4$ | 63 |
| X | $1.4 \times 10^5$ | $2.4 \times 10^4$ | 83 |

The results recorded in Table II with respect to $H_2S$-forming bacteria are consistent with the findings for the total bacteria load recorded in Table I.

EXAMPLE III

The dual component dentifrice composition of the present invention was also found to control volatile sulfur compound (VSC) formation in clinical breath VSC study involving the same human subjects described in Example I and Example II. Breath-odor was measured using a Halimeter™ at baseline and at four hours after brushing the teeth for one minute and swishing the slurry for 30 seconds. The results recorded in Table III are consistent with data represented in Table II indicating a greater reduction in breath VSC's responsible for oral malodor when compared to comparative compositions in which enzymes were not used in combination with Triclosan.

TABLE III

Clinical study involving oral malodor reduction.

| Composition | Baseline [VSC] in ppb* | 5 Hours Post Brushing [VSC] in ppb | % Reduction of Malodor |
|---|---|---|---|
| Placebo | 270 | 270 | 0 |
| C | 180 | 130 | 31 |
| X | 380 | 100 | 66 |

*ppb = parts per billion

The invention claimed is:

1. A dual component antiplaque dentifrice composition effective to reduce plaque and oral malodor comprising a first component comprised of an orally acceptable aqueous vehicle containing a humectant, an abrasive and a nonionic antibacterial agent and a second dentifrice component comprised of an orally acceptable aqueous vehicle containing a humectant, an abrasive and a proteolytic enzyme, the first and second components being simultaneously combined for application to the teeth, the first and second components being physically segregated prior to use, the components when combined and mixed upon application to teeth providing an antiplaque effect with a superior antimalodor benefit.

2. The composition of claim 1 wherein the abrasive is a silica abrasive having an oil absorption value less than 100 cc/100 g silica.

3. The composition of claim 2 wherein the low oil absorption silica abrasive is present in the dentifrice composition at a concentration of about 5 to about 40% by weight of the composition.

4. The composition of claim 1 wherein the proteolytic enzyme is papain.

5. The composition of claim 1 wherein the proteolytic enzyme is present in the dentifrice in combination with a lipase.

6. The composition of claim 1 wherein the proteolytic enzyme is present in the dentifrice composition in combination with a lipase and glucoamylase.

7. The composition of claim 6 wherein each enzyme is present in the composition at a concentration of about 0.02 to about 5.0% by weight of the composition.

8. The composition of claim 1 wherein the nonionic antibacterial agent is Triclosan.

* * * * *